United States Patent [19]

Kamishita

[11] Patent Number: 4,543,251

[45] Date of Patent: Sep. 24, 1985

[54] GEL PREPARATIONS FOR EXTERNAL APPLICATION

[75] Inventor: Takuzo Kamishita, Takatsuki, Japan

[73] Assignee: Toko Yakuhin Industry Co., Ltd., Osaka, Japan

[21] Appl. No.: 559,730

[22] Filed: Dec. 9, 1983

[51] Int. Cl.$^4$ ............ A61K 31/19; A61K 31/60; A61K 31/61; A61K 33/78

[52] U.S. Cl. .................... 424/81; 514/162; 514/567

[58] Field of Search ............. 424/81, 317, 230, 334

[56] References Cited

U.S. PATENT DOCUMENTS 3,749,773  7/1973  Ninga ............................ 424/81
4,309,414  1/1982  Inagi et al. ..................... 424/81

Primary Examiner—Stanley J. Friedman
Attorney, Agent, or Firm—Stiefel, Gross, Kurland & Pavane

[57] ABSTRACT

A gel preparation for external application by being prepared from diclofenac sodium as the active ingredient, water, lower alkanols and glycols as medium, a carboxyvinyl polymer as gelating agent, a weak basic substances and optionally adding peppermint oil, l-menthol or salicylic acid ester as auxiliary agent.

7 Claims, 4 Drawing Figures

GEL PREPARATIONS FOR EXTERNAL APPLICATION

BACKGROUND OF THE INVENTION

1. Field of the Invention

The present invention relates to gel preparations for external application containing diclofenac sodium as active ingredient and having good stability and nice feeling on use.

2. Description of the Prior Art

Diclofenac sodium is a derivative of phenylacetic acid represented by the formula:

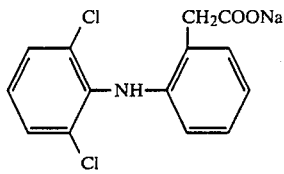

which is a non-steroid drug soluble in water and alcohols having excellent antiinflammatory and analgetic effects. For the present, it is used only in the form of oral preparations or suppositories and shows excellent antiinflammatory and analgetic effects. However, side effects such as stomach and intestines trouble, liver trouble and kidney trouble, are at issue, especially in the case of the oral administration. Therefore, antiinflammatory and analgetic preparations which are absorbed cutaneously without showing such side effects are desired.

In this regard, a gel preparation for external application containing indomethacin, a non-steroid drug, is known (Japanese Patent Laid-open No. Sho 53(1978)-81616). In this preparation, however, there is a question of stability and there is a defect that its yellow color due to the color of indomethacin itself soils clothes as it is applied on the skin. Thus, the inventor of the present invention has found preparations for external application which consist of a solution comprising another non-steroid compound having antiinflammatory and analgetic effects, at least one of peppermint oil and salicylic acid ester in an amount sufficient to dissolve the non-steroid compound and a base for external application (Japanese Patent Application No. Sho 56(1981)-128032). However, only water-insoluble compounds having antiinflammatory and analgetic effects may be used in such preparations.

SUMMARY OF THE INVENTION

The present invention provides gel preparations for external application characterized by being prepared from diclofenac sodium as the active ingredient, water, lower alkanols and glycols as medium, a carboxyvinyl polymer as gelating agent and a weak basic substance as neutralizing agent. The gel preparations for external application of this invention have good stability and nice feeling on use and show excellent antiinflammatory and analgetic effects by cutaneous absorption.

DESCRIPTION OF THE PREFERRED EMBODIMENTS

Figure 1:
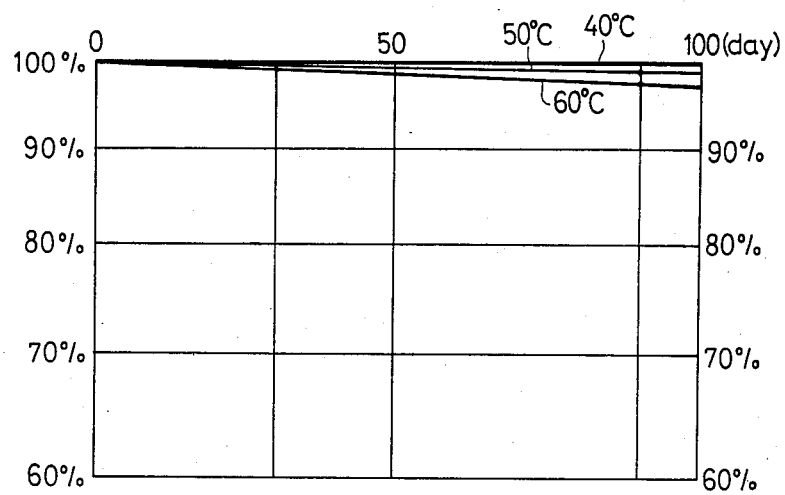
FIG. 1 is a graph showing changes with the lapse of time in the amount of diclofenac sodium contained in the preparation of Example 1 of the present invention.

The content of diclofenac sodium, the active ingredient, in the gel preparation of the present invention is usually 0.3 to 3.0% by weight, preferably, 0.5 to 2.0% by weight of the preparation.

As the medium for the active ingredient, water, lower alkanols and glycols are used.

It is possible to prepare a stable gel preparation of diclofenac sodium using as medium a combination of water and lower alkanols or a combination of water and glycols. However, when water and a lower alkanol are used, absorption of the active ingredient diclofenac sodium is not good, because the preparation gets dry so easily that diclofenac sodium crystallizes out on the surface of the skin. On the other hand, when water and a glycol are used as medium, it is necessary to use the glycol in an amount of at least 30% or more, in consideration of irritation which may be caused by pH on the skin. Nevertheless, if a glycol is used for the gel preparation in an amount of 30% or more, the preparation does not get dry well as applied on the skin. Moreover, the irritation on the skin by the glycol still remains as a problem.

Therefore, it is necessary to use a combination of water, lower alkanols and glycols.

The medium employed in the preparation of the present invention is used in an amount sufficient at least to dissolve the active ingredient, and constitutes the whole preparation together with the gelating agent, the neutralizing agent, the active ingredient, etc.

The ratio by weight of water to organic solvents in the medium is, for example, from 8:2 to 4:6. It is preferred that water is 80% by weight or less, lower alkanols are 60% by weight or less and glycols are 40% by weight or less of the medium. The preferred proportions by weight of the medium used in the present invention are water: lower alkanols: glycols of approximately 60:30:10.

As the lower alkanols, there can be mentioned methanol, ethanol, propanol, iso-propanol, butanol and the like. Among these, ethanol and iso-propanol are preferred.

As the glycols, ethylene glycol, propylene glycol and 1,3-butylene glycol are mentioned. The preferred among these are propylene glycol and 1,3-butylene glycol.

The most preferable combination for the medium of the above three solvents is water: ethanol: propylene glycol or water: ethanol: 1,3-butylene glycol.

Carboxyvinyl polymers used as the gelating agent are hydrophilic polymers obtained by polymerization of acrylic acid as the main component. It is desirable to use a commercial product. As commercially available products, there can be mentioned Hiviswako 103, Hiviswako 104, and Hiviswako 105 from Wakojunyakukogyo K.K. in Japan, Carbopol 934, Carbopol 940 and Carbopol 941 from Goodrich Chemical Co. in U.S.A., and the like.

In the preparations of the present invention, weak basic substances are used as the neutralizing agent in such amount as to adjust the preparation almost to neutrality, that is, to a pH of 6-8, preferably, a pH of 6.5–7.5. An amount of, for example, 0.1–5% by weight of the preparation is sufficient for this purpose.

As the weak basic substances, aliphatic amines are preferred. The aliphatic amines include primary, secondary and tertiary alkanolamines and primary, secondary and tertiary alkylamines. As concrete examples of the alkanolamines, there can be mentioned monoethanolamine, diethanolamine, diisopropanolamine, triethanolamine, triisopropanolamine, etc. As the alkylamines are mentioned dimethylamine, diethylamine, trimethylamine, triethylamine and the like. Especially preferred among these are triethanolamine and diisopropanolamine.

Use of such a weak basic substance as the neutralizing agent is one of the characteristic features of the present invention. It has been established that use of a strong base such as sodium hydroxide as the neutralizing agent is improper. Comparing carboxyvinyl polymers with diclofenac in the form of free acid, the acidity of the former is stronger than that of the latter. However, carboxyvinyl polymers are by themselves weak acids. Accordingly, when a strong base such as sodium hydroxide is used as the neutralizing agent, the pH value increases to about 9. Although it is possible to prepare gel preparations of diclofenac sodium using a gelating agent under such condition, the strong basicity (pH value of about 9) is undesirable for preparations for external application because it causes irritation on the skin.

On the other hand, when gel preparations of diclofenac sodium are prepared without neutralizing the carboxyvinyl polymer with sodium hydroxide, the free acid of diclofenac is formed in the resulting gel preparations since the sodium ion of diclofenac sodium combines with the acidic carboxyvinyl polymer even if the polymer is at a pH of about 7. Although diclofenac in the form of the sodium salt is stable, diclofenac itself is hardly soluble and loses stability in the preparations with time.

Further, to the gel preparation of the present invention, at least one of peppermint oil, l-menthol, methyl salicylate, ethyl salicylate and glycol monosalicylate may be added, if desired. Peppermint oil and l-menthol impart a cool feeling to the skin, and salicylic acid derivatives accelerate cutaneous absorption of the active ingredient. They are applied as an inductive stimulant in the case of pain complaints and increase the analgetic effects. These auxiliary agents are added to the gel preparations usually in an amount of 0.5 to 5% by weight.

Although the method of preparing the gel preparations of the present invention is not limited, they can be prepared, for example, according to the following techniques: Diclofenac sodium is dissolved in a lower alkanol. To the solution obtained are added an aqueous solution of a carboxyvinyl polymer and glycol, while stirring. Then, a neutralizing agent is added to the solution, while stirring, in such amount as to adjust the pH of the resulting gel preparation to about 6–8. Thus, the gel preparation of the present invention is obtained.

The gel preparation of the present invention can also be prepared by adding an aqueous solution of a carboxyvinyl polymer to a solution obtained by dissolving diclofenac sodium in a mixture of a lower alkanol and a glycol, while stirring, and then adding a neutralizing agent to the resulting solution while stirring.

To the gel preparation of the present invention, additives known in the art, such as aromatic agents, antiseptic agents, coloring agents, etc., may be added in small amounts, besides the salicylic acid esters as mentioned above, if so desired. However, good preparations are usually obtained without the necessity to add such additives.

The gel preparations of the present invention thus obtained have good stability. They do not show any change in viscosity at high temparatures or any crystalization at low temperatures. Moreover, they adhere well to the skin and spread very well. Further, they do not impart a sticky feeling and they dry easily.

In the following, the present invention is illustrated by giving examples of the preparations of the present invention and Comparative Examples of preparations having similar compositions and low pH values. However, the invention shall not be limited to these examples.

EXAMPLE 1

Diclofenac sodium (1 g) was dissolved in 95% ethanol (30 g) while stirring. On the other hand, propylene glycol (10 g), 4% aqueous solution (25 g) of a carboxyvinyl polymer Carbopol 940 and purified water (20 g) were mixed uniformly by stirring, and triethanolamine (1.5 g) was added to the mixture while continuing the stirring. To the gel base thus prepared, the alcoholic solution of diclofenac sodium previously prepared was added and the whole was adjusted to 100 g by further adding purified water. After stirring well, a gel preparation having a viscosity of 20,000 centipoise and a pH of 7.15 was obtained.

EXAMPLE 2

Diclofenac sodium (0.5 g) was dissolved in 95% ethanol (25 g) while stirring. On the other hand, 1,3-butylene glycol (20 g), 4% aqueous solution (25 g) of Carbopol 940 and purified water (20 g) were mixed uniformly by stirring, and triethanolamine (1.5 g) was added to the mixture while continuing the stirring. To the gel base thus prepared, the alcoholic solution of diclofenac sodium previously prepared was added and the whole was adjusted to 100 g by further adding purified water. After stirring well, a gel preparation having a viscosity of 22,000 centipoise and a pH of 7.15 was obtained.

EXAMPLE 3

Diclofenac sodium (3.0 g) and l-menthol (0.5 g) were dissolved in 95% ethanol (40 g) by stirring. On the other hand, propylene glycol (10 g), 4% aqueous solution (25 g) of Carbopol 940 and purified water (15 g) were mixed uniformly by stirring, and diisopropanolamine (3.0 g) was added to the mixture while continuing the stirring. To the gel base thus prepared, the alcoholic solution of diclofenac sodium previously prepared was added and the whole was adjusted to 100 g by further adding purified water. After stirring well, a gel preparation having a viscosity of 17,000 centipoise and a pH of 7.20 was obtained.

COMPARATIVE EXAMPLE 1

Diclofenac sodium (1.0 g) and peppermint oil (3.0 g) were dissolved in 95% ethanol (40 g) by stirring. Separately, 3% solution (20 g) of Carbopol 940 in propylene glycol, 4% aqueous solution (25 g) of Carbopol 940, citric acid (0.3 g) and purified water (8.0 g) were mixed uniformly by stirring, and triethanolamine (0.05 g) was added to the mixture while continuing the stirring. To the gel base thus prepared, the alcoholic solution of diclofenac sodium and peppermint oil prepared previously was added and the whole was adjusted to 100 g by further addition of purified water. After stirring well, a gel preparation having a viscosity of 22,000 centipoise and a pH of 5.2 was obtained.

COMPARATIVE EXAMPLE 2

Diclofenac sodium (1.0 g) was dissolved in 95% ethanol (40 g) by stirring. Separately, 3% solution (20 g) of Carbopol 940 in propylene glycol, 4% aqueous solution (25 g) of Carbopol 940 and purified water (10 g) were mixed uniformly by stirring, and triethanolamine (0.05 g) was added to the mixture while continuing the stirring. To the gel base thus prepared, the alcoholic solution of diclofenac sodium prepared previously was added and the whole was adjusted to 100 g by further addition of purified water. After stirring well, a gel preparation having a viscosity of 23,000 centipoise and a pH of 5.4 was obtained.

COMPARATIVE EXAMPLE 3

Diclofenac sodium (1.0 g) was dissolved in 95% ethanol (20 g) by stirring. Separately, 3% solution (40 g) of Carbopol 940 in propylene glycol, 4% aqueous solution (10 g) of Carbopol 940 and purified water (25 g) were mixed uniformly by stirring, and triethanolamine (0.8 g) was added to the mixture while continuing the stirring. To the gel base thus prepared, the alcoholic solution of diclofenac sodium previously prepared was added and the whole was adjusted to 100 g by further adding purified water. After stirring well, a gel preparation having a viscosity of 21,000 centipoise and a pH of 5.8 was obtained.

Figure 2:
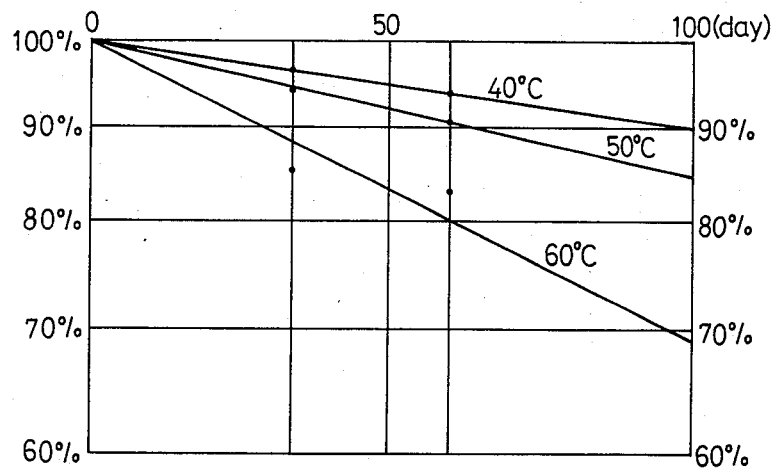
FIGS. 2 to 4 are graphs showing changes with the lapse of time in the amount of diclofenac sodium contained in the preparations of Comparative Examples 1 to 3, respectively.
Figure 3:
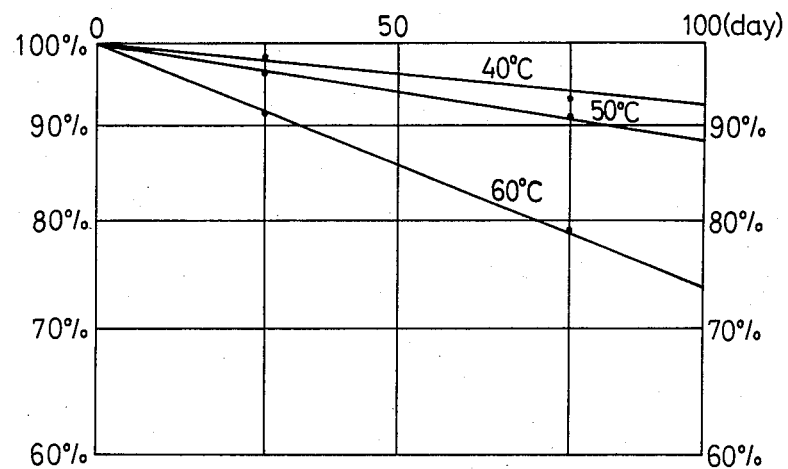
Figure 4:
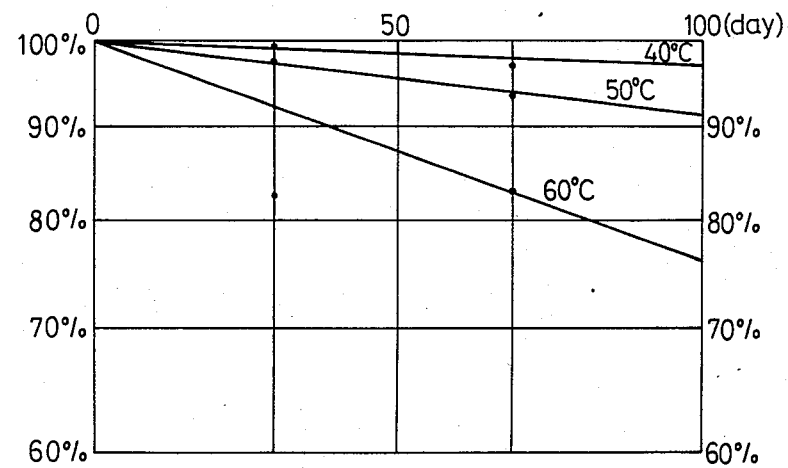

Next, comparison between the gel preparations of the above Examples and the gel preparation of the Comparative Examples was effected with regard to the stability of diclofenac sodium with time. More precisely, the content of diclophenac sodium in each preparation was measured just after the preparation was obtained and after the lapse of a preseribed time, according to the method of analysis described hereinafter. The changes with time in the content of diclofenac sodium in the preparation of Example 1 are shown in FIG. 1, and those of the preparations of Comparative Examples 1 to 3 are shown in FIGS. 2 to 4, respectively (abscissa: days elapsed, ordinate: percentages of the active ingredient contained in the preparation, that just after the preparation is obtained being taken as 100%).

It is apparent from these Figures that the preparation of Example 1 has significantly greater stability with time, as compared with the preparations of the Comparative Examples.

The measurement of the content of diclofenac sodium in the above gel preparation was effected by extracting diclofenac sodium with ethanol, isolating diclofenac sodium from the extract by high-performance liquid chromatography (column: Lichrosorb RP$_{18}$, developing agent: methanol/water/acetic acid-600:400:5, room temperature), and determining the ultraviolet absorbance (254 nm).

What is claimed is:

1. A gel preparation for external application comprising diclofenac sodium as the active ingredient and present in amount of 0.3 to 3.0% by weight; a medium comprising water, a lower alkanol selected from the group consisting of methanol, ethanol, iso-propanol, butanol; and a glycol selected from the group consisting of ethylene glycol, propylene glycol and 1,3-butylene glycol, the medium being present in an amount at least sufficient to dissolve the active ingredient, the ratio of water to the combination of the lower alkanol and glycol being from about 8:2 to 4:6; a carboxyvinyl polymer selected from the group consisting of the hydrophilic polymers obtained by polymerization of acrylic acid, and present in an amount sufficient to gel the preparation; and an aliphatic amine, present in an amount sufficient to adjust the pH to about 6–8.

2. A gel preparation as claimed in claim 1, wherein the aliphatic amine is a primary, secondary or tertiary alkanolamine, or a primary, secondary or tertiary alkylamine.

3. A gel preparation as claimed in claim 1, wherein the weak basic substance is triethanolamine or diisopropanolamine.

4. A gel preparation as claimed in claim 1, which further contains peppermint oil, l-methol or salicyclic acid ester added there to as auxiliary agent.

5. A gel preparation as claimed in claim 4, wherein the salicylic acid ester is methyl salicylate, ethyl salicylate or glycol salicylate.

6. A gel preparation as claimed in claim 1, wherein the ratio by weight of water: lower alkanol: glycol in the medium is about 60:30:10.

7. The gel preparation of claim 1, wherein the aliphatic amine is present in an amount of from 0.1–5% by weight of the preparation.

* * * * *